United States Patent [19]

Fuchs et al.

[11] 4,082,769
[45] Apr. 4, 1978

[54] BENZOTHIOXANTHENES

[75] Inventors: Otto Fuchs, Frankfurt am Main; Helmut Tröster, Konigstein, Taunus, both of Germany

[73] Assignee: Hoechst Aktiengesellschaft, Frankfurt am Main, Germany

[21] Appl. No.: 772,269

[22] Filed: Feb. 25, 1977

[30] Foreign Application Priority Data

Feb. 27, 1976 Germany .................... 2607966

[51] Int. Cl.² .................... C07D 335/04
[52] U.S. Cl. .................... 260/328; 8/179
[58] Field of Search .................... 260/328

[56] References Cited

U.S. PATENT DOCUMENTS 3,356,687  12/1967  Fuchs et al. .................... 260/328

Primary Examiner—Cecilia M. S. Jaisle
Attorney, Agent, or Firm—Curtis, Morris & Safford

[57] ABSTRACT

Treating compounds of the formula

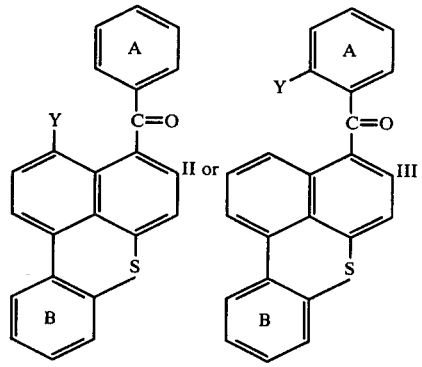

in which the nuclei marked "A" and "B" can be substituted by halogen, lower alkyl, lower alkoxy or phenyl, with acid binding agents at elevated temperatures in polar organic solvents yields compounds of the formula

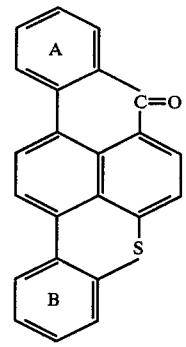

I in which A and B have the same meaning. The products are dyestuffs of high brillancy, pure shades, high fluorescence, excellent tinctorial strength and good fastness to light.

13 Claims, No Drawings

BENZOTHIOXANTHENES

The present invention provides compounds of the following formula

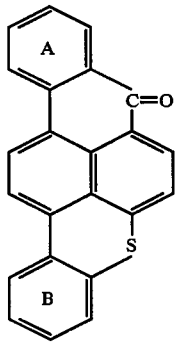

I wherein the benzene nuclei A and B may be substituted by halogen atoms, phenyl or lower alkyl or lower alkoxy groups. By "lower", there is to be understood in this respect and hereinafter that these radicals contain from 1 to 6, preferably from 1 to 4, and especially 1 or 2, carbon atoms.

The present invention provides furthermore a process for the manufacture of the compounds of formula I, which comprises treating compounds of the following formulae II or III

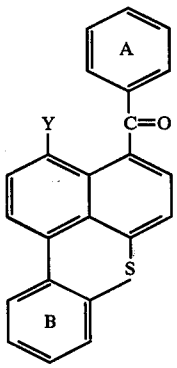

II

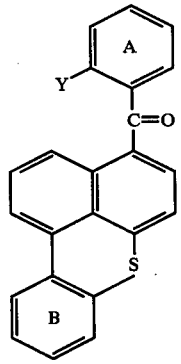

III wherein the benzene nuclei A and B may be substituted as indicated for formula I, and Y is a chlorine or bromine atom, with acid-binding agents in polar organic solvents at elevated temperature.

The compounds of formula II used as starting materials may be prepared for example as follows: 1,5-dihalonaphthalene is reacted according to Friedel-Crafts with optionally substituted benzoic acid chlorides, and the 1,5-dihalo-6-aroylnaphthalenes obtained are converted, with splitting-off of hydrogen halide, to 1-(2'-aminoaryl-mercapto)-5-halo-6-aroylnaphthalenes, which latter ones may be converted, after diazotation, in known manner by boiling with, for example, copper sulfate solution, to the 3-halo-4-aroyl-benzo[k,l]thioxanthenes of formula II.

The compounds of formula III may be prepared in analogous manner, by using 1-chloro- or 1-bromo-naphthalene instead of 1,5-dihalo-naphthalene, and by employing optionally benzoic acid chlorides having a chlorine or bromine atom in o-position for the Friedel-Crafts reaction.

The compounds of formula I may be advantageously obtained from compounds of formula II or III in the following manner: the compounds of formula II or III are heated to temperatures of from about 140° to about 250° C, preferably 150° to 200° C, in a polar solvent and in the presence of acid-binding agents, until the splitting-off of hydrogen halide which proceeds with high yields is complete. The products may be directly isolated from the solvent, optionally after previous concentration or dilution with another solvent. The products are obtained in the form of crystals, and, if necessary, they may be easily purified by recrystallization, especially from a polar solvent such as dimethyl formamide.

Suitable polar solvents for splitting off the hydrogen halide are for example monohydric alcohols or polyols, especially lower alkanols, partially alkylated polyols, especially lower alkyl or hydroxyalkyl ethers of ethyleneglycol, carboxylic acid mono- and dialkyl-amides having lower alkyl groups and derived from lower alkanecarboxylic acids or lactams, such as N-methyl-pyrrolidone. In the case where the boiling point of the solvent used is below the reaction temperature, the reaction is carried out by heating in a pressure vessel, preferably provided with an agitator.

Suitable acid-binding agents are for example alkali metal or alkaline earth metal hydroxides or carbonates. The hydrogen halide is more easily split off when benzene- or p-toluene-sulfonamide is added.

The manufacturing process of the invention may be compared next to the preparation of benzanthrone from [2-chlorophenyl-naphthyl-(1)]-ketone

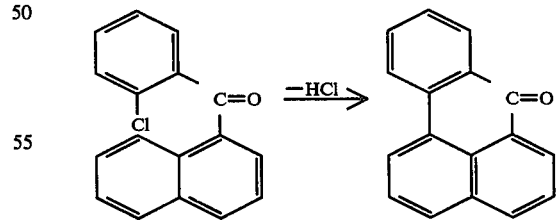

according to U.S. Pat. No. 1,803,205, which is carried out at 350° – 450° C in a nitrogen current in the presence of a catalyst impregnated with potassium carbonate. It was surprising to observe that in contrast to this method, the reaction according to this invention which yields a benzanthrone system too may be carried out at considerably lower temperatures.

The products obtained in the new process are dyestuffs which excel in the dyeing of plastic materials in the mass, especially thermoplastics, for example polyvinyl chloride, polystyrene, polymethacrylate, polyolefins or copolymers of styrene, butadiene, acrylonitrile and/or acrylic acid esters. They are furthermore suitable for the dyeing of synthetic fibers of linear polyesters in an aqueous bath or in the spinning mass. They are distinguished by an extraordinary brilliancy of the golden yellow to orange shades, intense fluorescence, high tinctorial strength and good fastness to light. Because of their fluorescence, they are suitable for increasing the brilliancy of other less pure dyestuffs when blended therewith.

The following examples illustrate the invention; the temperatures being indicated in ° C.

EXAMPLE 1

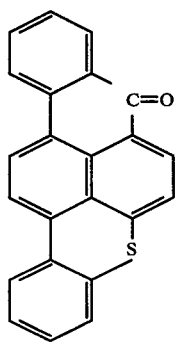

49.6 g of 3-chloro-4-benzoyl-benzo[k,l]thioxanthene, 12.5 g of finely ground potassium carbonate and 28.0 g of p-toluene-sulfonamide are heated to boiling for 10 hours in 300 ml of dimethyl formamide while distilling off the water formed by the reaction and a small amount of dimethyl formamide and with substitution of the amount of solvent distilled off. After cooling to 80°, the reaction mixture is diluted with 300 ml of methanol. The crystal suspension formed is filtered off, the filter residue is washed with methanol and water, and dried. Yield: 40.5 g.

After fine distribution, the product obtained dyes polystyrene, polymethacrylate or unplasticized PVC in the mass in a full golden orange shade with intense fluorescence. In a finely distributed form, the dyestuff dyes polyester fabrics in the presence of surface-active substances in an aqueous bath at a temperature above 100° in a brilliant golden yellow and fluorescing shade having a good fastness to light.

When a spinning mass of polyesters is dyed, filaments having a brilliant golden yellow shade with intense fluorescence are obtained.

EXAMPLE 2

95 g of 3-chloro-4-benzoyl-benzo[k,l]thioxanthene and 12 g of sodium hydroxide in 2000 ml of ethanol are heated at 180° for 3 hours in a pressure vessel with agitation. After cooling, filtration is carried out, and the filter residue is washed with water and ethanol, and dried. Yield: 80 g.

When methanol, propanol, isopropanol, butanol or isobutanol are used instead of ethanol, the reaction product is obtained with the same yields and the same purity degree.

EXAMPLE 3

37 g of 3-chloro-4-benzoyl-benzo[k,l]thioxanthene, 6 g of potassium hydroxide and 500 ml of ethyl diglycol (monoethyl ether of 2-(2'-hydroxyethoxy)-ethanol) are boiled for 30 minutes with agitation, while distilling off the water of reaction and a small amount of solvent. The reaction product isolated by filtration after cooling is washed with water and dried. Yield: 28.5 g.

Instead of ethyl diglycol, there may be used alternatively methyl diglycol or partially alkylated lower diols, for example methyl glycol, ethyl glycol or butyl glycol, the yields being the same as above.

EXAMPLE 4

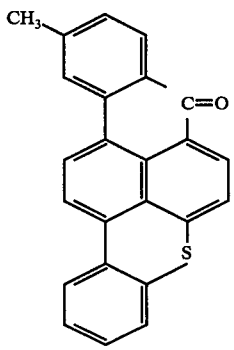

11.7 g of 3-chloro-4-(4'-methyl-benzoyl)-benzo[k,l]thioxanthene, 3.6 g of finely pulverulent sodium carbonate and 120 ml of N-methylpyrrolidone are heated to boiling for 1 hour with agitation and while distilling off the water formed in the reaction. After cooling to 70°, 300 ml of methanol are added. The crystal suspension is filtered off at room temperature, washed with water and methanol, and dried. Yield: 7.9 g.

In a finely distributed form, the reaction product is suitable for dyeing thermoplastics, where it yields brilliant golden orange dyeings with intense fluorescence.

EXAMPLE 5

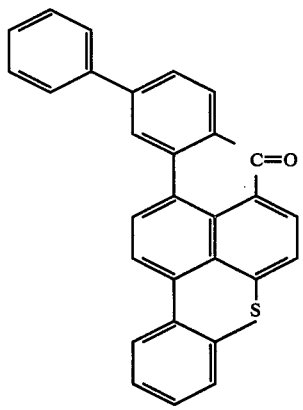

7.5 g of 3-chloro-4-(4'-phenylbenzoyl)-benzo[k,l]thioxanthene, 3.7 g of p-toluenesulfonamide and 1.4 g of finely pulverulent potassium carbonate in 50 ml of dimethyl formamide are refluxed for 15 hours with agitation. After cooling, the crystal suspension is filtered off, and the filter residue is washed with methanol and water. Yield: 6.3 g. The dyestuff obtained dyes polystyrene, polymethacrylate and polyolefins in a full, fluorescent golden orange shade having a good fastness to light.

As indicated in the Examples 2 to 4, the 3-chloro- or 3-bromo-4-aroyl-benzo[k,l]thioxanthenes of the formula

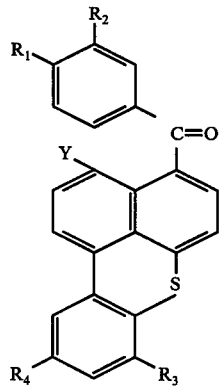

are converted to the corresponding closed ring dyestuffs of the following formula

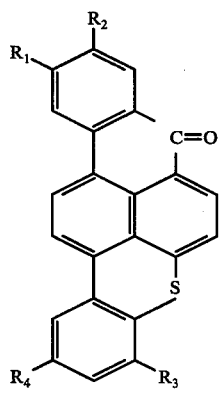

wherein $R_1$ through $R_4$ are as defined in the following Table.

| Example | $R_1$ | $R_2$ | $R_3$ | $R_4$ | prepaed according to Example | Color in unplasticized PVC |
|---|---|---|---|---|---|---|
| 6 | H | CH$_3$ | H | H | 4 | golden orange |
| 7 | Cl | H | H | H | 4 | orange |
| 8 | H | H | H | CH$_3$ | 2 | orange |
| 9 | H | H | H | Cl | 4 | golden orange |
| 10 | H | H | Cl | H | 4 | golden yellow |
| 11 | CH$_3$ | H | H | CH$_3$ | 3 | orange |
| 12 | H | H | H | OCH$_3$ | 3 | orange |

EXAMPLE 13

37 g of 4-(2'-chloro-benzoyl)-benzo[k,l]thioxanthene are reacted according to the indications of Example 4 with 12 g of sodium carbonate in 400 ml of N-methylpyrrolidone. The reaction product obtained with a yield of 25 g is composed as the compound obtained according to Example 1 and, after recrystallization from dimethyl formamide, it has the same properties.

The same result is obtained when the equivalent amount of the corresponding bromine compound is used for the reaction.

We claim:
1. A compound of the formula

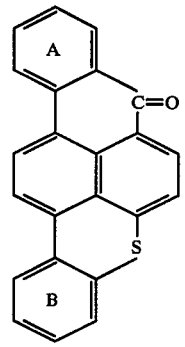

in which the nuclei marked A and B can be substituted by halogen, alkyl or alkoxy of 1 to 6 carbon atoms or phenyl.

2. A compound as claimed in claim 1, wherein the substituents are chlorine, bromine, alkyl or alkoxy of 1 to 4 carbon atoms or phenyl.

3. A compound as claimed in claim 1, wherein the substituents are chlorine, alkyl or alkoxy of 1 or 2 carbon atoms or phenyl.

4. A compound as claimed in claim 1, wherein each nucleus marked A and B is unsubstituted or substituted by one substituent selected from methyl, methoxy, chlorine and phenyl.

5. A compound as claimed in claim 1 having the formula

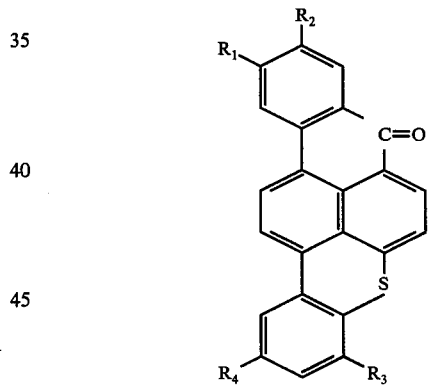

in which $R_1$, $R_2$, $R_3$ and $R_4$ are hydrogen, methyl, methoxy, chlorine or phenyl.

6. The compound as claimed in claim 5, wherein $R_1$, $R_2$, $R_3$ and $R_4$ are hydrogen.

7. The compound as claimed in claim 5, wherein $R_1$ is methyl and $R_2$, $R_3$ and $R_4$ are hydrogen.

8. The compound as claimed in claim 5, wherein $R_1$ is phenyl and $R_2$, $R_3$ and $R_4$ are hydrogen.

9. The compound as claimed in claim 5, wherein $R_2$ is methyl and $R_1$, $R_3$ and $R_4$ are hydrogen.

10. The compound as claimed in claim 5, wherein $R_4$ is methyl and $R_1$, $R_2$ and $R_3$ are hydrogen.

11. The compound as claimed in claim 5, wherein $R_1$ and $R_4$ are methyl and $R_2$ and $R_3$ are hydrogen.

12. A compound as claimed in claim 5, wherein $R_1$ or $R_3$ or $R_4$ is chlorine and the other substituents are hydrogen.

13. The compound as claimed in claim 5, wherein $R_4$ is methoxy and $R_1$, $R_2$ and $R_3$ are hydrogen.